US012782366B2

(12) United States Patent
Shen et al.

(10) Patent No.: US 12,782,366 B2
(45) **Date of Patent: *Nov. 3, 2026**

(54) PROTEIN ANTIGEN COMBINATION, DETECTION METHOD AND TESTING KIT USING THE SAME

(71) Applicant: SHANGHAI ZHONGQI BIOTECHNOLOGY CO., LTD., Shanghai (CN)

(72) Inventors: Lu Shen, Shanghai (CN); Qihui Wu, Shanghai (CN); Kun Yin, Shanghai (CN); Yonghong Zou, Shanghai (CN); Liqin Cao, Shanghai (CN)

(73) Assignee: SHANGHAI ZHONGQI BIOTECHNOLOGY CO., LTD., Shanghai (CN)

( * ) Notice: Subject to any disclaimer, the term of this patent is extended or adjusted under 35 U.S.C. 154(b) by 1203 days.

This patent is subject to a terminal disclaimer.

(21) Appl. No.: 17/459,780

(22) Filed: Aug. 27, 2021

(65) Prior Publication Data

US 2021/0396769 A1 Dec. 23, 2021

Related U.S. Application Data

(63) Continuation of application No. PCT/CN2020/085224, filed on Apr. 17, 2020.

(30) Foreign Application Priority Data

Jan. 15, 2020 (CN) ......................... 202010039229.1

(51) Int. Cl.
*G01N 33/68* (2006.01)
*G01N 33/532* (2006.01)

(52) U.S. Cl.
CPC ....... *G01N 33/6896* (2013.01); *G01N 33/532* (2013.01); *G01N 2800/2821* (2013.01); *G01N 2800/52* (2013.01)

(58) Field of Classification Search
None
See application file for complete search history.

(56) References Cited

U.S. PATENT DOCUMENTS 9,145,446 B2 9/2015 Epenetos et al.
9,650,627 B1 * 5/2017 Rosenthal .......... C12N 15/1024
10,124,110 B2 11/2018 Dedig et al.
11,435,361 B2 9/2022 Nagele
11,571,485 B2 * 2/2023 Ruoslahti ........... G01N 33/6896
2003/0109420 A1 * 6/2003 Valkirs ................... G01N 33/53 435/7.1
2008/0287357 A1 11/2008 Epenetos et al.
2013/0157888 A1 6/2013 Nagele
2014/0094445 A1 4/2014 Vakayalapati et al.
2014/0315736 A1 10/2014 Nagele
2014/0364328 A1 * 12/2014 Nagele ............... G01N 33/6896 506/18
2016/0250409 A1 9/2016 Dedig et al.
2018/0318303 A1 11/2018 Jack et al.
2019/0086429 A1 3/2019 Nagele
2020/0081019 A1 3/2020 Veiga Herreros et al.
2020/0309795 A1 10/2020 Nagele
2020/0340990 A1 10/2020 Nagele

FOREIGN PATENT DOCUMENTS

CN 101194017 A 6/2008
CN 103154736 A 6/2013
CN 105555784 A 5/2016
CN 108138234 A 6/2018
CN 109738653 A 5/2019
CN 110850104 A 2/2020
EP 3376230 A 9/2018
EP 3978930 A1 4/2022
JP 2016-523256 A 8/2016
WO WO-9839448 A2 * 9/1998 ........... A01C 23/024
WO WO-02097031 A2 * 12/2002 ............. C07K 14/47
WO WO-2005012875 A2 * 2/2005 ............. C12Q 1/485
WO WO-2006020269 A2 * 2/2006 ....... G01N 33/56972
WO WO-2010021755 A2 * 2/2010 ......... A61K 38/1709
WO WO-2012170993 A2 * 12/2012 ................ A61P 1/18
WO 2013/010003 A1 1/2013
WO WO-2016044271 A2 * 3/2016 ......... A01K 67/0273

(Continued)

OTHER PUBLICATIONS

UniProt. P10636 • TAU_HUMAN. https://www.uniprot.org/uniprotkb/P10636/entry#sequences. Retrieved on Oct. 24, 2024. (Year: 2024).*
UniProt. P78563 • RED1_HUMAN. https://www.uniprot.org/uniprotkb/P78563/entry. Retrieved on Oct. 24, 2024 (Year: 2024).*
UniProt. P38936 • CDN1A_HUMAN. https://www.uniprot.org/uniprotkb/P38936/entry. Retrieved on Oct. 24, 2024 (Year: 2024).*
UniProt. 075937 • DNJC8_HUMAN. https://www.uniprot.org/uniprotkb/075937/entry. Retrieved on Oct. 24, 2024 (Year: 2024).*
UniProt. Q15109 • RAGE_HUMAN. https://www.uniprot.org/uniprotkb/Q15109/entry. Retrieved on Oct. 24, 2024 (Year: 2024).*
UniProt. Q8IXJ9 • ASXL1_HUMAN. https://www.uniprot.org/uniprotkb/Q8IXJ9/entry. Retrieved on Oct. 24, 2024/ (Year: 2024).*
UniProt. P10809 • CH60_HUMAN. https://www.uniprot.org/uniprotkb/P10809/entry. Retrieved on Oct. 24, 2024/ (Year: 2024).*

(Continued)

*Primary Examiner* — Christopher L Chin
*Assistant Examiner* — Fernando Ivich
(74) *Attorney, Agent, or Firm* — Flener IP & Business Law

(57) ABSTRACT

A protein antigen combination for detecting Alzheimer's disease autoantibodies in human serum sample and an application thereof are disclosed. The protein antigen combination includes at least two protein fragments selected from the following proteins: MAPT, ADARB1, P21, DNAJC8, RAGE, ASXL1, and JMJD2D. Based on the protein antigen composition, a kit for diagnosis, especially for early diagnosis of Alzheimer's disease or its related risks, can be prepared. By using the protein antigen composition provided by the invention, early Alzheimer's disease can be quickly and accurately diagnosed, which has important practical significance.

12 Claims, No Drawings

Specification includes a Sequence Listing.

(56) References Cited

FOREIGN PATENT DOCUMENTS

| | | | | | |
|---|---|---|---|---|---|
| WO | WO-2017015660 | A1 * | 1/2017 | .......... | A61K 31/175 |
| WO | 2017/106338 | A1 | 6/2017 | | |
| WO | 2018/094076 | A1 | 5/2018 | | |
| WO | WO-2018085050 | A1 * | 5/2018 | ............ | A61K 33/30 |
| WO | WO-2020051555 | A1 * | 3/2020 | ......... | A61K 31/7088 |

OTHER PUBLICATIONS

Cleveland Clinic. Parkinson's Disease. Last reviewed on Apr. 15, 2022 https://my.clevelandclinic.org/health/diseases/8525-parkinsons-disease-an-overview. Retrieved online Nov. 6, 2024. (Year: 2022).*

Hasegawa et al. Front Neurosci. Jan. 10, 2018;11:743. doi: 10.3389/fnins.2017.00743 (Year: 2018).*

Gelsi-Boyer et al. Journal of Hematology & Oncology 2012, 5:12 http://www.jhoonline.org/content/5/1/12 (Year: 2012).*

National Library of Medicine, *Homo sapiens* ASXL transcriptional regulator 1 (ASXL1), transcript variant 1, mRNA (retrieved online https://www.ncbi.nlm.nih.gov/nuccore/NM_015338.5 on Feb. 24, 2025). (Year: 2025).*

National Library of Medicine, *Homo sapiens* dystroglycan 1 (DAG1), transcript variant 2, mRNA (retrieved online https://www.ncbi.nlm.nih.gov/nuccore/NM_004393.5 on Feb. 25, 2025) (Year: 2025).*

Riessland et al. Cell Stem Cell vol. 25, Issue 4, Oct. 3, 2019, pp. 514-530.e8 (Year: 2019).*

Mann et al. Nat Commun. Nov. 10, 2017;8(1):1403. doi: 10.1038/s41467-017-01096-0 (Year: 2017).*

National Library of Medicine, *Homo sapiens* heat shock protein family D (Hsp60) member 1 (HSPD1), transcript variant 1, mRNA; nuclear gene for mitochondrial product (retrieved online https://www.ncbi.nlm.nih.gov/nuccore/NM_002156.5 on Feb. 28, 2025) (Year: 2025).*

National Library of Medicine, *Homo sapiens* dystroglycan 1 (DAG1), transcript variant 2, mRNA (retrieved online https://www.ncbi.nlm.nih.gov/nuccore/NM_004393.5 on Feb. 28, 2025) (Year: 2025).*

Yin et al. Brain Research 1265 (2009) 158-170 doi: 10.1016/j.brainres.2009.01.058 (Year: 2009).*

Barresi and Campbell J Cell Sci (2006) 119 (2): 199-207 https://doi.org/10.1242/jcs.02814 (Year: 2006).*

UniProt DAG1 (retrieved online https://www.uniprot.org/uniprotkb/Q14118/entry#ptm_processing on Aug. 6, 2025) (Year: 2025).*

National Library of Medicine (NLM) DNAJC8 (retrieved online https://www.ncbi.nlm.nih.gov/nuccore/NM_014280 on Feb. 11, 2026), (Year: 2026).*

NLM RAGE (retrieved online https://www.ncbi.nlm.nih.gov/nuccore/NM_001136.5 on Feb. 11, 2026) (Year: 2026).*

NLM MAPT (retrieved online https://www.ncbi.nlm.nih.gov/nuccore/NM_016835.4 on Feb. 11, 2026) (Year: 2026).*

NLM ADARB1(retrieved online https://www.ncbi.nlm.nih.gov/nuccore/NM_001112.4 on Feb. 11, 2026) (Year: 2026).*

Nlm P21 (retrieved online https://www.ncbi.nlm.nih.gov/nuccore/NM_000389 on Feb. 11, 2026) (Year: 2026).*

NLM JMJD2D (retrieved online https://www.ncbi.nlm.nih.gov/nuccore/NM_018039.3 on Feb. 11, 2026) (Year: 2026).*

NLM (retrieved online https://www.ncbi.nlm.nih.gov/nuccore/NM_015833.1 on Feb. 12, 2026) (Year: 2026).*

NLM (retrieved online https://www.ncbi.nlm.nih.gov/nuccore/BC033159.1 on Feb. 12, 2026) (Year: 2026).*

NLM (retrieved online https://www.ncbi.nlm.nih.gov/nuccore/BC064984.1 on Feb. 12, 2026) (Year: 2026).*

NLM (retrieved online https://www.ncbi.nlm.nih.gov/nuccore/NM_018039.2 on Feb. 12, 2026) (Year: 2026).*

Papuc et al. PLoS ONE 10(1): e0115480. doi:10.1371/journal.pone.0115480. Published: Jan. 28, 2015 (Year: 2015).*

NLM (retrieved online https://www.ncbi.nlm.nih.gov/nuccore/NM_002156.5 on Feb. 12, 2026) (Year: 2026).*

International Search Report; International Searching Authority/CN dated Sep. 15, 2020; International Application No. PCT/CN2020/085224; 7 pgs.; National Intellectual Property Administration, PRC (ISA/CN); Beijing, China.

Oliveira-Junior et al., "Epitope Fingerprinting for Recognition of the Polyclonal Serum Autoantibodies of Alzheimer's Disease," BioMed Research International; publication date: 2015; vol. 2015, article ID 267989, 8 pgs.; Hindawi Publishing Corp.

Krestova et al., "Changes in concentrations of tau-reactive antibodies are dependent on sex in Alzheimer's disease patients," J. Neuroimmun.; publication date: 2018; vol. 322 (2018) 1-8; Elsevier B.V.

Marcello et al., "Reduced levels of IgM autoantibodies against N-truncated pyroglutamate Aβ in plasma of patients with Alzheimer's disease," Neurobiol. Aging; publication date: 2011; vol. 32 (2011) 1379-1387; Elsevier B.V.

Sim et al., "High-throughput epitope profiling of antibodies in the plasma of Alzheimer's disease patients using random peptide microarrays," Scientific Reports; Mar. 14, 2019; 9:4587; Springer Nature.

* cited by examiner

PROTEIN ANTIGEN COMBINATION, DETECTION METHOD AND TESTING KIT USING THE SAME

CROSS-REFERENCE TO RELATED APPLICATIONS

This application is a continuation of International Pat. Appl. No. PCT/CN2020/085224, filed Apr. 17, 2020, pending, which claims the benefit of Chinese Patent Application No. 202010039229.1, filed on Jan. 15, 2020, incorporated herein by reference in its entirety.

SEQUENCE LISTING

The present application incorporates by reference a Sequence Listing in the ASCII text file identified by the file name "Sequence Listing.txt", created on Jun. 20, 2025, and having a size of 13, 637 bytes.

FIELD OF THE INVENTION

The present disclosure belongs to the field of biological detection, in particular to a protein antigen combination for detecting Alzheimer's disease autoantibodies in human serum sample and an application thereof.

BACKGROUND

Alzheimer's disease (AD) is a progressive neurodegenerative disease characterized by memory and cognitive dysfunction. It frequently occurs in the elderly, with a slow and irreversible course. According to the development of cognitive dysfunction, Alzheimer's disease can be divided into early, middle and late stages. In the early stage, the patients have no obvious symptoms, most of them only show forgetfulness and anxiety, so it is difficult to detect or diagnose. In the middle stage, there will be chaotic symptoms, the patients' character and habits will change, and memory will also be confused. In the later stage, the patients completely show dementia, have no ability to take care of themselves, and eventually die of a variety of secondary diseases.

The current diagnostic methods of Alzheimer's disease include: 1. Early and significant episodic memory dysfunction; 2. Middle temporal gyrus atrophy; 3. Abnormal cerebrospinal fluid biomarkers, including decreased concentration of amyloid beta 1-42 (Aβ 1-42), increased concentration of total Tau protein, increased concentration of phosphorylated Tau protein, or a combination of the three; 4. Specificity of PET functional neuroimaging showed that glucose metabolic rate in bilateral temporal and parietal lobes decreased; 5. AD related autosomal dominant mutation was found in lineal relatives. However, because the early symptoms are not obvious, and it is difficult to distinguish the middle stage from other diseases, there are still significant problems of missed diagnosis and misdiagnosis in the diagnosis of Alzheimer's disease. Therefore, an effective tool for the diagnosis or staging of AD is urgently needed.

An autoantibody is an antibody produced by the individual's immune system against the individual'S autoprotein (i.e., own protein) antigen. Normally, the immune system produces antibodies in response to exogenous proteins or substances in the body, but sometimes it also recognizes one or more endogenous components of the body, resulting in the production of autoantibody. There has been a lot of evidence that there are a variety of autoantibodies in the serum involved in neurological diseases and syndromes. As far as Alzheimer'S disease is concerned, many literatures have reported that patients have high titers of autoantibodies against non-brain and brain-related targets, including those binding to neurons.

The detection of antibodies in serum is a very mature technology, which makes it possible to accurately detect the autoantibodies of Alzheimer's disease, and then use the autoantibodies of Alzheimer's disease in serum as the detection target to achieve the purpose of diagnosis. For example, Chinese patent application Publication No. CN103154736A disclosed a series of proteins, which suggested that these proteins could potentially be used as antigens binding to autoantibodies of Alzheimer's disease, so they could be used as diagnostic indicators of Alzheimer's disease.

However, the protein antigens disclosed in CN103154736A are extremely numerous, so it is still necessary to select the proteins that can be used in combination as a protein antigen combination to detect the possible autoantibodies of Alzheimer's disease in the serum of subjects with high specificity and sensitivity, so as to provide a practical means for the diagnosis of Alzheimer's disease. Moreover, even for a single protein antigen, the binding of the full-length protein to the corresponding autoantibodies of Alzheimer's disease may be very weak, resulting in poor detection, detection failure, or even misdiagnosis. Therefore, whether used alone or in combination, it is very important to screen out specific protein antigen combination, or specific region or fragment in the protein to effectively bind and detect the corresponding autoantibodies.

SUMMARY OF THE INVENTION

An object of the invention is to provide a protein antigen combination for detecting Alzheimer's disease autoantibodies in human serum sample and its application.

In order to realize the above object of the invention, embodiments of the invention include an antigen combination that includes at least two protein fragments selected from the following proteins: microtubule associated protein tau (MAPT), Adenosine Deaminase RNA Specific B1 (ADARB 1), protein p21 (WAF1/CIP1) (P21), DnaJ (Hsp40) homolog subfamily C member 8 (DNAJC8), receptor for advanced glycation endproducts (RAGE), additional sex combs-like protein 1 (ASXL1) and JMJD2D histone demethylase (JMJD2D).

In some embodiments, the protein fragment sequence is selected from one or more of the following sequences:

The MAPT protein fragment shown in SEQ ID NO: 1;
The ADARB1 protein fragment shown in SEQ ID NO: 2;
The P21 protein fragment shown in SEQ ID NO: 4;
The DNAJC8 protein fragment shown in SEQ ID NO: 6;
The RAGE protein fragment shown in SEQ ID NO: 7;
The ASXL1 protein fragment shown in SEQ ID NO:8; and
The JMJD2D protein fragment shown in SEQ ID NO: 9.

Furthermore, the protein antigen combination may comprise any one of the following: a heat shock protein 60 (HSP60) and dystroglycan (DAG) fragment. The protein sequences may be as follows: the HSP60 protein sequence shown in SEQ ID NO:3; and the DAG protein fragment sequence shown in SEQ ID NO: 5.

In some embodiments, the protein antigen combination includes the MAPT protein fragment, the ADARB1 protein fragment and the HSP60 protein.

In other embodiments, the protein antigen combination includes the DNAJC8 protein fragment, the RAGE protein fragment and the ASXL1 protein fragment.

In other embodiments, the protein antigen combination includes the JMJD2D protein fragment, the P21 protein fragment and the DAG protein fragment.

In yet other embodiments, the protein antigen combination includes (i) the MAPT protein fragment, the HSP60 protein and the DNAJC8 protein fragment; (ii) the ADARB1 protein fragment, the RAGE protein fragment and the ASXL1 protein fragment; or (iii) the HSP60 protein, the RAGE protein fragment and the P21 protein fragment.

Accordingly, the protein antigen combination can be applied in detecting Alzheimer's disease.

Accordingly, a kit for detecting Alzheimer's disease can be prepared by using the protein antigen combination.

Accordingly, the sample used in the kit may be whole blood or serum.

Preferably, an antigen for detecting Alzheimer's disease is a MAPT protein fragment, and its sequence may be as shown in SEQ ID NO:1.

Another antigen for detecting Alzheimer's disease is an ADARB1 protein fragment, and its sequence may be shown in SEQ ID NO: 2.

Another antigen for detecting Alzheimer's disease is a P21 protein fragment, and its sequence may be shown in SEQ ID NO: 4.

Another antigen for detecting Alzheimer's disease is a DNAJC8 protein fragment, and its sequence may be shown in SEQ ID NO: 6.

Another antigen for detecting Alzheimer's disease is a RAGE protein fragment, and its sequence may be shown in SEQ ID NO: 7.

Another antigen for detecting Alzheimer's disease is an ASXL1 protein fragment, and its sequence may be shown in SEQ ID NO: 8.

Yet another antigen for detecting Alzheimer's disease is a JMJD2D protein fragment, and its sequence may be shown in SEQ ID NO: 9.

The invention has the following beneficial effects: The invention provides a protein antigen composition for detecting the autoantibodies of Alzheimer's disease, wherein the protein antigen or its fragment can be prepared by artificial synthesis. For example, the synthetic protein antigen or the coding DNA of its fragment is used as the template, the primers are designed, and the gene fragment of the protein antigen or its fragment is cloned into an expression plasmid by PCR, enzyme digestion, ligation and other molecular cloning means. At the same time, HIS and c-myc tags can be selectively added to the N-terminal of protein antigen or its fragment.

The protein antigen combination provided by the invention has the following uses:

(1) Testing the presence or presence level of autoantibodies against the above protein antigen combination in biological samples from the subject, so as to determine whether the subject has Alzheimer's disease; predicting whether the subject has a risk of Alzheimer's disease; evaluating the progress of Alzheimer's disease; or determining whether the subject has the risk of recurrence of Alzheimer's disease. The biological samples can be serum, plasma, whole blood, saliva, oral mucosa swab, urine, lymph, cerebrospinal fluid, etc. According to the specific situation, the biological samples can be pretreated by extraction, dilution, enrichment and other means. The method of use is various, simple and easy to operate.

When the protein antigen combination provided by the invention is used for the above test, the presence or presence level of the autoantibody is tested by binding or interacting the protein or fragment in the protein antigen combination with the corresponding autoantibody that may exist.

(2) The protein antigen combination provided by the invention can also be used for preparing Alzheimer's disease autoantibody detection reagents or Alzheimer's disease diagnosis reagents. It should be understood that the protein antigen combination can also be used to prepare an Alzheimer's disease autoantibody detection kit. The kit can refer to the method and reagent preparation when using the protein antigen combination for Alzheimer's disease autoantibody detection in embodiments of the invention, and can also be adjusted according to the needs.

In conclusion, the invention provides a protein antigen combination, which can be used for the detection or diagnosis of Alzheimer's disease, especially for early detection or diagnosis; it can also be used for the disease risk prediction of Alzheimer's disease; and it can be further prepared as a related reagent or kit according to the needs.

DETAILED DESCRIPTION

The present application is further explained in combination with specific embodiments. Unless otherwise specified, the experimental methods used in the following examples are conventional methods; the materials and reagents used can be obtained from commercial channels; the data obtained are the average values obtained after at least three repetitions, and the data obtained from each repetition are valid data.

Example 1: Construction, Expression and Purification of Recombinant Vector of Protein Antigen 1. Protein antigen selection. 115 antigen proteins highly related to Alzheimer's disease were selected for construction, expression and purification. For brevity, only 50 representative ones of them are represented in this paper, and their respective database IDs are shown in Table 1.

TABLE 1

| Database ID of proteins to be tested | | | |
|---|---|---|---|
| Protein name | Database ID | Protein name | Database ID |
| RABPT5 | NM_004703.6 | C20orf96 | BC051762.1 |
| RAGE | NM_001136.5 | CCL12 | NM_011331.2 |
| MAPT | NM_016835.4 | ARPP-19 | NM_006628.4 |
| MBP | NM_001025101.2 | BMF | BC069328.1 |
| MOG | NM_002433.4 | CA13 | BC052602.1 |
| PTCD2 | NM_024754.5 | CENTD2 | BC056401.1 |
| POMC | NM_000939.4 | CSAG3A | BC007228.1 |
| DNAJC8 | NM_014280 | CSNK2A2 | NM_001896.2 |
| MRPL34 | NM_023937.3 | DDX54 | BC001132.1 |
| CENTA2 | NM_018404 | FCGR3A | BC036723.1 |
| HSP60 | NM_002156.5 | FGF16 | NM_003868.1 |
| ADARB1 | NM_001112.4 | HSPC111 | BC040106.1 |
| LENG1 | NM_024316.2 | IER3 | NM_003897.2 |
| ASXL1 | NM_015338.5 | IMPACT | NM_018439.1 |
| RPL23A | NM_000984.6 | PIN4 | NM_006223.1 |
| EDRK | NP_001171558.1 | ROBO3 | BC008623.1 |
| P21 | NM_000389 | SERPINE2 | BC042628.1 |
| GDF11 | NM_005811 | SPT16 | BC021561._1 |
| CCL2 | NM_002982.4 | STK25 | NM_006374.2 |
| JMJD2D | NM_00018039.3 | TARBP2 | NM_004178.3 |

TABLE 1-continued

| Database ID of proteins to be tested | | | |
|---|---|---|---|
| Protein name | Database ID | Protein name | Database ID |
| GFAP | NM_002055.5 | TBC1D21 | NM_153356.1 |
| DAG | NM_004393.5 | TIPIN | BC000870.1 |
| CTGF | NM_001901.2 | TTLL7 | BC048970.1 |
| SH3GL2 | NM_003026.3 | VCY | BC056508.1 |
| RABEP2 | BC058900.1 | POLB | NM_002690.1 |

2. Construction and expression of antigen recombinant vector. The target protein antigens were screened from the 50 proteins in Table 1. Using a human cDNA library (purchased from INVITROGEN®) or whole gene synthetic DNA as template, primers were designed respectively, and the full-length gene of the proteins was cloned into the pET28 plasmid by PCR, enzyme digestion, ligation and other molecular cloning methods. At the same time, HIS and c-myc tags were added to the N-terminal of the proteins to form fusion proteins. The recombinant expression vector was identified by DNA sequencing and confirmed to contain the correct protein gene fragment. It should be noted that the added tag(s) is only convenient for identification and extraction of protein, and does not have a decisive impact on the function of protein as antigen. When using, it is not necessary to add a label or add other labels as needed.

The recombinant plasmid containing the protein gene fragment was transformed into competent cells of *E. coli* BL21 (DE3), and the clones were selected and inoculated into LB medium, and then shaking-cultured at 37° C. to grow the bacteria. When the *E. coli* BL21 (DE3) density reached $OD_{600}$ about 0.8, the temperature was reduced to 16° C., and 0.1 mM isopropylthio—β—d-galactoside (IPTG) was added to each LB medium to induce the expression overnight.

3. Purification of protein antigen. The expression-induced bacteria were collected by centrifugation and rinsed twice with PBS. The pyrolysate (5-10 mL pyrolysate per g bacteria) was used to suspend and disperse the bacteria. The bacteria cell was broken by ice bath and ultrasonic wave (ultrasonic power 200 W, broken for 5 s, rest for 5 s). After crushing, centrifugation at 13000 rpm, 10° C. was conducted for, and the supernatant was purified by Ni column affinity chromatography and molecular sieve chromatography. SDS-PAGE electrophoresis was used to confirm the molecular weight and purity of the protein. Bradford method was used to determine the concentration, and then the protein was stored at −80° C. for standby. The purified protein was obtained.

Example 2: Screening Candidate Antigens from Proteins to be Tested

1. The solutions and reagents used in this example are as follows:

(1) The coating buffer was PBS buffer, pH=7.4. The preparation method is as follows: 3.58 g $Na_2HPO_4·12H_2O$, 0.23 g $KH_2PO_4·2H_2O$, 0.2 g KCl and 8.0 g NaCl are accurately weighed and dissolved in a relatively small amount of water, then diluted with water to 1 L.

(2) Blocking solution/sample diluent/antibody diluent: dissolve 10 g BSA (bovine serum albumin) in the coating buffer, and dilute with water to 1 L.

(3) Detergent: It should be prepared when using. Add 0.5% Tween20 (V/V) to the coating buffer before use, pH=7.4.

(4) TMB chromogenic agent, purchased from KPL company.

(5) Termination solution: 1M hydrochloric acid.

2. Coating the protein onto a solid phase: Dilute the purified protein to be tested in example 1 to 5 μg/mL with the coating buffer, add it to 96-well plate, 50 μL for each well, and coat it at 4° C. overnight. The next day, pour out the solution, dry it, and wash it three times with detergent, 200 μL per well each time. Then 200 μL blocking solution was added to each well, and incubated at room temperature for 1 h, then the blocking solution was poured out and dried, and then washed with the detergent for three times, 200 μL per well each time, and dried again to obtain the solid coated antigen in 96 well plate.

3. Adding the sample to be tested: The human serum to be tested was diluted 100 times with sample diluent and then added to the 96-well plate containing the protein to be tested, and 50 μL of the diluted sample to be tested is added to each well. Then, the 96-well plate was placed on the microplate shaker and incubated at room temperature for 1h; then, the plate was dried, washed with the detergent three times, 200 μL per well each time, and then dried again.

4. Adding the enzyme-labeled second antibody: 1.0 mg/mL horseradish peroxidase-labeled recombinant Goat anti-human immunoglobulin G antibody (purchased from Jackson immune research Inc.) was diluted 20000 times with the antibody diluent, and then added to the 96-well plate treated in step 3, 50 μL for each well. Then, the 96-well plate was placed on the microplate shaker, incubated at room temperature for 0.5 h, then dried, washed three times with the detergent, 200 μL per well each time, and dried again.

5. Color reaction and optical density reading: In the 96-well plate treated in step 4, 50 μL TMB chromogenic agent was added to each well, and the shaking time was 15s. The reaction was kept away from light for 15 min at room temperature, and then 50 μL termination solution was added. Then the absorbance value at 450 nm was read by a microplate reader to obtain the detection signal(S) of each sample.

6. Sensitivity and specificity analysis: 180 positive samples (serum of patients diagnosed with Alzheimer's disease) and 180 negative samples (serum of healthy subjects) were taken respectively. The detection signal (S) of each sample was determined according to the above method (absorption value of 450 nm wavelength). Negative samples were taken as negative reference samples. The mean (M, average value) and standard deviation (SD) of the detection signals(S) of all negative reference samples were calculated, and M+3SD was taken as the cut-off value. The samples with a detection signal(S)≥cut off value (S≥M+3SD) were regarded as positive; the samples with a detection signal(S)<cut off value (S<M+3SD) were regarded as negative.

The specificity and sensitivity were calculated based on the positive and negative results of the samples. Among them, specificity refers to the proportion of healthy subjects whose samples are correctly determined as negative, that is, the number of negative samples which are correctly determined as negative divided by the total number of negative samples. Sensitivity refers to the proportion of samples of patients with Alzheimer's disease that are correctly determined to be positive, that is, the number of positive samples divided by the total number of positive samples. The sensitivity and specificity of using each protein to be tested as antigen for sample detection are calculated, and the results are shown in Table 2.

TABLE 2

Sensitivity and specificity of proteins to be tested as antigens

| protein | suscepti-bility | Specificity | protein | susceptibility | Specificity |
|---|---|---|---|---|---|
| RABPT5 | 20.56% | 83.33% | C20orf96 | 7.78% | 79.44% |
| RAGE | 28.33% | 84.44% | CCL12 | 11.11% | 93.33% |
| MAPT | 36.67% | 88.89% | ARPP-19 | 18.89% | 76.11% |
| MBP | 27.78% | 89.44% | BMF | 16.67% | 82.22% |
| MOG | 20.56% | 80.56% | CA13 | 8.89% | 81.67% |
| PTCD2 | 24.44% | 84.44% | CENTD2 | 4.44% | 99.44% |
| POMC | 21.11% | 85.56% | CSAG3A | 11.67% | 72.22% |
| DNAJC8 | 31.11% | 86.67% | CSNK2A2 | 17.22% | 79.44% |
| MRPL34 | 26.67% | 87.22% | DDX54 | 0.56% | 76.11% |
| CENTA2 | 27.22% | 82.78% | FCGR3A | 0.56% | 95% |
| HSP60 | 35.56% | 88.33% | FGF16 | 4.44% | 84.44% |
| ADARB1 | 36.67% | 87.78% | HSPC111 | 18.89% | 72.22% |
| LENG1 | 24.44% | 87.22% | IER3 | 19.44% | 90% |
| ASXL1 | 27.78% | 86.11% | IMPACT | 16.11% | 74.44% |
| RPL23A | 22.22% | 83.33% | PIN4 | 5.56% | 95% |
| EDRK | 26.67% | 85.56% | ROBO3 | 8.33% | 85% |
| P21 | 36.11% | 84.44% | SERPINE2 | 15% | 91.11% |
| GDF11 | 25% | 84.44% | SPT16 | 10% | 97.22% |
| CCL2 | 25.56% | 86.67% | STK25 | 19.44% | 80% |
| JMJD2D | 27.78% | 86.11% | TARBP2 | 11.11% | 73.89% |
| GFAP | 23.89% | 85% | TBC1D21 | 10% | 77.78% |
| DAG | 30.56% | 85.56% | TIPIN | 2.78% | 85.56% |
| CTGF | 12.22% | 86.67% | TTLL7 | 19.44% | 84.44% |
| SH3GL2 | 18.33% | 78.89% | VCY | 10% | 97.78% |
| RABEP2 | 23.89% | 68.89% | POLB | 14.44% | 80.56% |

7. The proteins with sensitivity≥20% and specificity≥75% were selected as candidate antigens. The screening results are shown in Table 3.

TABLE 3

Display of candidate antigens selected from the proteins to be tested

| Candidate antigen | susceptibility | Specificity |
|---|---|---|
| MAPT | 36.67% | 88.89% |
| ADARB1 | 36.67% | 87.78% |
| HSP60 | 35.56% | 88.33% |
| P21 | 36.11% | 84.44% |
| DAG | 30.56% | 85.56% |
| DNAJC8 | 31.11% | 86.67% |
| RAGE | 28.33% | 84.44% |
| ASXL1 | 27.78% | 86.11% |
| JMJD2D | 27.78% | 86.11% |
| EDRK | 26.67% | 85.56% |
| MBP | 27.78% | 89.44% |
| MRPL34 | 26.67% | 87.22% |
| CENTA2 | 27.22% | 82.78% |
| PTCD2 | 24.44% | 84.44% |
| LENG1 | 24.44% | 87.22% |
| GDF11 | 25.00% | 84.44% |
| CCL2 | 25.56% | 86.67% |
| GFAP | 23.89% | 85.00% |
| RPL23A | 22.22% | 83.33% |
| POMC | 21.11% | 85.56% |
| RABPT5 | 20.56% | 83.33% |
| MOG | 20.56% | 80.56% |

Example 3: active sites screening of candidate antigens 1. The amino acid sequences and structures of the candidate antigens obtained in example 2 were analyzed. After a large number of preliminary tests, different sequence fragments and epitopes were selected from each candidate antigen. The selected sequence fragments or full length is shown in Table 4.

TABLE 4

Sequence fragments intercepted from each candidate antigen

| Candidate antigen | Starting and ending positions of amino acids | Candidate antigen | Starting and ending positions of amino acids |
|---|---|---|---|
| MAPT | 2-288 | DNACJ8 | 2-253 |
| | 502-758 | | 114-253 |
| | 526-691 | | 2-140 |
| ADARB1 | 1-299 | RAGE | 1-404 |
| | 299-741 | | 23-54 |
| | 678-741 | | 338-404 |
| HSP60 | 1-355 | ASXL1 | 1-84 |
| | 302-573 | | 100-209 |
| | 1-573 | | 641-684 |
| P21 | 42-164 | JMJD2D | 1-523 |
| | 2-164 | | 223-523 |
| | 55-160 | | 1-160 |
| EDRK | 1-35 | GDF11 | 25-298 |
| | 20-59 | | 42-407 |
| | 1-62 | | 299-407 |
| MBP | 120-304 | CCL2 | 45-120 |
| | 1-304 | | 1-120 |
| | 1-135 | | 25-100 |
| MRPL34 | 1-92 | GFAP | 120-423 |
| | 1-46 | | 100-175 |
| | 47-92 | | 251-436 |
| CENTA2 | 1-220 | RPL23A | 1-163 |
| | 105-320 | | 81-163 |
| | 1-381 | | 9-163 |
| PTCD2 | 151-268 | POMC | 61-301 |
| | 38-120 | | 1-301 |
| | 195-320 | | 113-301 |
| LENG1 | 1-264 | RABPT5 | 1-433 |
| | 1-120 | | 101-399 |
| | 121-260 | | 187-433 |
| MOG | 1-252 | DAG | 1-9 |
| | 30-183 | | |
| | 30-252 | | |

2. According to the method of example 1, the expression vector of each protein fragment in Table 4 was constructed, expressed and purified to obtain the constructed protein fragment, and then the sensitivity and specificity of each constructed protein fragment as antigen were detected according to the method of example 2. As in example 1, although some labels are added to each protein fragment, the purpose of adding labels is to facilitate extraction and recognition, and does not have a material impact on the function of protein fragment as antigen. The purpose of the invention can be realized by using the protein before and after adding the label. In actual use, a person having ordinary skill in the art can select whether to add the label and the type of the label according to the need. Therefore, the full text of the invention only provides the protein sequence before labeling. The test results are shown in Table 5.

TABLE 5

Comparison table of sensitivity and specificity of optimized candidate antigen fragments

| Candidate antigen | Starting and ending positions of amino acids | susceptibility | Specificity |
|---|---|---|---|
| MAPT | 2-288 | 11.11% | 83.33% |
| | 502-758 | 40.56% | 90.00% |
| | 526-691 | 19.44% | 80.00% |
| ADARB1 | 1-299 | 24.44% | 72.22% |
| | 299-741 | 42.78% | 83.89% |
| | 678-741 | 39.44% | 93.33% |
| HSP60 | 1-355 | 15.56% | 84.44% |
| | 302-573 | 20.00% | 88.89% |
| | 1-573 | 38.33% | 95.00% |
| P21 | 42-164 | 27.78% | 88.89% |
| | 2-164 | 37.22% | 90.00% |
| | 55-160 | 30.56% | 89.44% |
| DAG | 1-9 | 35.56% | 90.00% |
| DNACJ8 | 2-253 | 32.22% | 81.67% |
| | 114-253 | 35.00% | 88.89% |
| | 2-140 | 50.00% | 55.56% |
| RAGE | 1-404 | 20.56% | 81.67% |
| | 23-54 | 33.89% | 88.33% |
| | 338-404 | 24.44% | 82.78% |
| ASXL1 | 1-84 | 33.33% | 90.00% |
| | 100-209 | 31.67% | 79.44% |
| | 641-684 | 32.78% | 82.22% |
| JMJD2D | 1-523 | 20.56% | 73.89% |
| | 223-523 | 23.89% | 77.78% |
| | 1-160 | 33.89% | 89.44% |
| EDRK | 1-35 | 21.11% | 77.78% |
| | 20-59 | 23.33% | 83.89% |
| | 1-64 | 32.22% | 90.00% |
| MBP | 120-304 | 32.22% | 87.22% |
| | 1-304 | 27.78% | 84.44% |
| | 1-135 | 26.11% | 85.56% |
| MRPL34 | 1-92 | 19.44% | 90.56% |
| | 1-46 | 23.89% | 81.67% |
| | 47-92 | 30.56% | 87.22% |
| CENTA2 | 1-220 | 22.78% | 80.00% |
| | 105-320 | 25.56% | 75.56% |
| | 1-381 | 30.00% | 88.89% |
| PTCD2 | 151-268 | 31.11% | 77.22% |
| | 38-120 | 28.89% | 91.11% |
| | 195-320 | 21.67% | 86.67% |
| LENG1 | 1-264 | 27.78% | 92.22% |
| | 1-120 | 25.00% | 85.00% |
| | 121-260 | 26.11% | 85.56% |
| GDF11 | 25-298 | 25.56% | 78.33% |
| | 42-407 | 27.78% | 92.78% |
| | 299-407 | 23.89% | 86.11% |
| CCL2 | 45-120 | 26.67% | 87.22% |
| | 1-120 | 10.56% | 91.11% |
| | 25-100 | 21.11% | 81.67% |
| GFAP | 120-423 | 26.11% | 89.44% |
| | 100-175 | 19.44% | 84.44% |
| | 251-436 | 26.11% | 75.00% |
| RPL23A | 1-163 | 8.89% | 92.22% |
| | 81-163 | 17.22% | 86.67% |
| | 9-163 | 25.56% | 88.33% |
| POMC | 61-301 | 23.89% | 87.22% |
| | 1-301 | 15.00% | 93.33% |
| | 113-301 | 20.56% | 82.78% |
| RABPT5 | 1-433 | 18.89% | 79.44% |
| | 101-399 | 16.67% | 84.44% |
| | 187-433 | 22.22% | 89.44% |
| MOG | 1-252 | 8.33% | 93.33% |
| | 30-183 | 20.00% | 83.33% |
| | 30-252 | 13.89% | 80.56% |

3. According to the results in Table 5, for some proteins, compared with the whole protein, the protein fragments obtained by intercepting specific amino acid sequence regions and corresponding optimization have better detection effect; for some antigens, the detection effect of whole protein is better than that of its fragments. This may be due to the inhibition of some protein fragments in some whole proteins during the binding or recognition of Alzheimer's disease-related sites.

According to the results in Table 5, nine full-length proteins or their fragments were further screened. The sensitivity of the selected full-length proteins or their fragments was more than 33%, and the specificity was more than 88%. They were used as candidate antigens to distinguish Alzheimer's disease patients and healthy subjects. The screening results are shown in Table 6.

TABLE 6

Comparison of sensitivity and specificity of each candidate antigen

| Candidate antigen | susceptibility | Specificity | Fragment or full length | Serial number |
|---|---|---|---|---|
| MAPT[502-758] | 40.56% | 90.00% | fragment | SEQ ID NO. 1 |
| ADARB1[678-741] | 39.44% | 93.33% | fragment | SEQ ID NO. 2 |
| HSP60[1-573] | 38.33% | 95.00% | overall length | SEQ ID NO. 3 |
| P21[2-164] | 37.22% | 90.00% | fragment | SEQ ID NO. 4 |
| DAG[1-9] | 35.56% | 90.00% | length | SEQ ID NO. 5 |
| DNAJC8[114-253] | 35.00% | 88.89% | fragment | SEQ ID NO. 6 |
| RAGE[23-54] | 33.89% | 88.33% | fragment | SEQ ID NO. 7 |
| ASXL4[1-84] | 33.33% | 90.00% | fragment | SEQ ID NO. 8 |
| JMJD2D[1-160] | 33.89% | 89.44% | fragment | SEQ ID NO. 9 |

Example 4: Display of Detection Effect of Candidate Antigens

1. According to the screening results in Table 6, different antigen combinations are selected from the candidate protein antigens. Based on the whole proteins corresponding to the candidate protein fragments of candidate groups 1-8, the corresponding whole protein combinations are set as control groups 1-8; according to the combinations 5 and 6 in Table 5 of patent CN109738653A, the control groups 9 and 10 are set respectively. The details are shown in Table 7. It should be noted that the inventor did not only carry out the combination test in Table 7; the inventor obtained the protein antigen combinations shown in Table 7 after a large number of preliminary tests, and only selected some combinations with better effect due to space limitation.

TABLE 7

Comparison of antigen combinations

| group | combination |
|---|---|
| Candidate group 1 | MAPT[502-758], ADARB1[678-741], HSP60[1-573] |
| Candidate group 2 | DNAJC8[114-253], RAGE[23-54], ASXL1[1-84] |
| Candidate group 3 | JMJD2D[1-160], P21[2-164], DAG[1-9] |
| Candidate group 4 | MAPT[502-758], DNAJC8[114-253], JMJD2D[1-160] |

TABLE 7-continued

| Comparison of antigen combinations | |
|---|---|
| group | combination |
| Candidate group 5 | MAPT[502-758], HSP60[1-573], DNAJC8[114-253] |
| Candidate group 6 | ADARB1[678-741], RAGE[23-54], ASXL1[1-84] |
| Candidate group 7 | HSP60[1-573], RAGE[23-54], P21[2-164] |
| Candidate group 8 | ADARB1[678-741], HSP60[1-573], ASXL1[1-84] |
| Candidate group 9 | MAPT[502-758], RAGE[23-54], JMJD2D[1-160] |
| Candidate group 10 | ADARB1[678-741], ASXL1[1-84], DAG[1-9] |
| Control group 1 | MAPT, ADARB1, HSP60 |
| Control group 2 | DNAJC8, RAGE, ASXL1 |
| Control group 3 | JMJD2D, P21, DAG |
| Control group 4 | MAPT, DNAJC8, JMJD2D |
| Control group 5 | MAPT, HSP60, DNAJC8 |
| Control group 6 | ADARB1, RAGE, ASXL1 |
| Control group 7 | HSP60, RAGE, P21 |
| Control group 8 | ADARB1, HSP60, ASXL1 |
| Control group 9 | RAGE, DNAJC8, HSP60, MRPL34, ADARB1, CCL2, MAPT, ASXL1, GDF11 |
| Control group 10 | RAGE, DNAJC8, HSP60, MRPL34, ADARB1, CCL2, MAPT, MBP, GDF11 |

2. According to Mini-Mental State Examination (MMSE), the patients with Alzheimer's disease and healthy subjects were scored. The subjects with scores of 27-30 were normal, the subjects with scores of 21-26 were mild (early), the subjects with scores of 10-20 were moderate (middle), and the subjects with scores of 0-9 were severe (late).

According to the MMSE score, 180 patients with Alzheimer's disease in the early stage, 90 patients in the middle stage and 90 patients in the late stage were selected as the test samples; 180 healthy subjects with normal MMSE score were selected as the samples of healthy subjects. According to the detection method of example 2, the sensitivity and specificity of the above samples were detected by using the protein antigen combinations of each group in Table 7 (it should be noted that the proteins used in the control group were whole proteins). The sensitivity and specificity in this embodiment are specifically overall specificity, overall sensitivity, early sensitivity, mid-term sensitivity and late sensitivity.

Among them, the definition method of positive and negative for early sensitivity, mid-term sensitivity and late sensitivity refers to example 2.

Early sensitivity refers to the proportion of 180 samples of patients with early Alzheimer's disease correctly determined as positive by the antigen combination, that is, the number of samples of patients with early Alzheimer's disease correctly determined as positive divided by the total number of samples of patients with early Alzheimer's disease; medium sensitivity refers to the proportion of 90 samples of patients with middle Alzheimer's disease correctly determined as positive, that is, in the middle stage, the number of positive samples from patients with Alzheimer's disease divided by the total number of samples from patients s with mid-term Alzheimer's disease; late sensitivity refers to the proportion of 90 samples from patients with late Alzheimer's disease correctly determined to be positive, that is, the number of positive samples from patients with late Alzheimer's disease divided by the total number of samples from patients with late Alzheimer's disease. Overall sensitivity refers to the proportion of 180 samples of patients with early Alzheimer's disease, 90 samples of patients with intermediate Alzheimer's disease and 90 samples of patients with advanced Alzheimer's disease that are correctly determined as positive, that is, the number of samples of all patients with Alzheimer's disease divided by the total number of samples of all patients with Alzheimer's disease; overall specificity refers to the proportion of 180 samples of healthy subjects that are correctly determined as negative, that is, in 180 healthy subjects, the number of negative healthy subjects divided by the total number of healthy subjects.

The results of antigen combination test of each group are shown in Table 8.

TABLE 8

| Comparison of antigen combination test results of each group | | | | | |
|---|---|---|---|---|---|
| group | Early sensitivity | Medium term sensitivity | Late sensitivity | Overall sensitivity | Overall specificity |
| Candidate group 1 | 94.44% | 88.89% | 93.33% | 92.78% | 90.00% |
| Candidate group 2 | 93.33% | 88.89% | 88.89% | 91.11% | 88.89% |
| Candidate group 3 | 94.44% | 84.44% | 91.11% | 91.11% | 88.33% |
| Candidate group 4 | 90.00% | 86.67% | 86.67% | 88.33% | 88.33% |
| Candidate group 5 | 92.22% | 88.89% | 91.11% | 91.11% | 90.00% |
| Candidate group 6 | 94.44% | 84.44% | 91.11% | 91.11% | 88.89% |
| Candidate group 7 | 93.33% | 91.11% | 80.00% | 89.44% | 90.00% |
| Candidate group 8 | 93.33% | 73.33% | 91.11% | 87.78% | 88.89% |
| Candidate group 9 | 74.44% | 88.89% | 91.11% | 82.22% | 88.33% |
| Candidate group 10 | 66.67% | 84.44% | 93.33% | 77.78% | 88.89% |
| Control group 1 | 77.78% | 66.67% | 80.00% | 75.56% | 83.33% |
| Control group 2 | 76.67% | 73.33% | 77.78% | 76.11% | 80.56% |
| Control group 3 | 80.00% | 62.22% | 80.00% | 75.56% | 77.78% |
| Control group 4 | 73.33% | 64.44% | 71.11% | 70.56% | 79.44% |
| Control group 5 | 75.56% | 66.67% | 75.56% | 73.33% | 80.00% |
| Control group 6 | 77.78% | 68.89% | 80.00% | 76.11% | 78.89% |
| Control group 7 | 78.89% | 68.89% | 77.78% | 76.11% | 77.78% |
| Control group 8 | 76.67% | 64.44% | 80.00% | 74.44% | 75.56% |
| Control group 9 | 83.33% | 77.78% | 82.22% | 81.67% | 87.22% |
| Control group 10 | 85.56% | 84.44% | 75.56% | 82.78% | 87.78% |

It can be seen from Table 8 that candidate groups 1-8 have higher sensitivity and specificity; the overall sensitivity is greater than 85%, and the overall specificity is greater than 88%. At the same time, compared with intermediate and late samples, the antigen combination provided by the invention has higher sensitivity in detecting early samples. Therefore, the invention provides a more accurate detection method for the diagnosis of Alzheimer's disease, especially for the early diagnosis.

In later application, one or more candidate antigen or antigen combinations provided by the invention can be selected as AD diagnostic kit according to needs.

What is claimed is:

1. A combination of separate protein antigens for diagnosis of Alzheimer's disease, comprising a microtubule associated protein tau (MAPT) fragment shown in SEQ ID NO: 1, an Adenosine Deaminase RNA Specific B1 (ADARB1) fragment shown in SEQ ID NO: 2, and a heat shock protein 60 (HSP60) shown in SEQ ID NO:3, wherein each protein fragment of the combination of separate protein antigens is fused to a heterologous tag.

2. A combination of separate protein antigens for diagnosis of Alzheimer's disease, comprising (1) a receptor for advanced glycation endproducts (RAGE) fragment shown in SEQ ID NO:7, (2) an additional sex combs-like protein 1 (ASXL1) fragment shown in SEQ ID NO: 8, and (3) a DnaJ (Hsp40) homolog subfamily C member 8 (DNAJC8) fragment shown in SEQ ID NO:6 or an Adenosine Deaminase RNA Specific B1 (ADARB1) fragment shown in SEQ ID NO:2, wherein each protein fragment of the combination of separate protein antigens is fused to a heterologous tag.

3. A combination of separate protein antigens for diagnosis of Alzheimer's disease, comprising a JMJD2D histone demethylase (JMJD2D) fragment shown in SEQ ID NO: 9, a protein p21 (WAF1/CIP1) (P21) fragment shown in SEQ ID NO:4, and a dystroglycan (DAG) fragment shown in SEQ ID NO:5, wherein each protein fragment of the combination of separate protein antigens is fused to a heterologous tag.

4. A kit for detecting Alzheimer's disease, comprising the combination of separate protein antigens according to claim 1, purified and prepared for detecting autoantibodies against at least one of the protein fragment in a biological sample;

a labeled anti-human antibody that binds to the autoantibodies; and a chromogenic agent that changes an absorbance of light at a predetermined wavelength in a test sample containing the combination of separate protein antigens, the autoantibodies and the labeled anti-human antibody.

5. The kit according to claim 4, wherein the biological sample is whole blood or serum.

6. The combination of separate protein antigens according to claim 1, wherein the heterologous tag comprises a HIS tag or a c-myc tag.

7. A kit for detecting Alzheimer's disease, comprising the combination of separate protein antigens according to claim 6, purified and prepared for detecting autoantibodies against at least one of the protein fragment in a biological sample;

a labeled anti-human antibody that binds to the autoantibodies; and a chromogenic agent that changes an absorbance of light at a predetermined wavelength in a test sample containing the combination of separate protein antigens, the autoantibodies and the labeled anti-human antibody.

8. The kit according to claim 7, wherein the biological sample is whole blood or serum.

9. A kit for detecting Alzheimer's disease, comprising the combination of separate protein antigens according to claim 3, purified and prepared for detecting autoantibodies against at least one of the protein fragment in a biological sample;

a labeled anti-human antibody that binds to the autoantibodies; and a chromogenic agent that changes an absorbance of light at a predetermined wavelength in a test sample containing the combination of separate protein antigens, the autoantibodies and the labeled anti-human antibody.

10. The kit according to claim 9, wherein the biological sample is whole blood or serum.

11. The combination of separate protein antigens according to claim 2, wherein the heterologous tag comprises a HIS tag or a c-myc tag.

12. The combination of separate protein antigens according to claim 3, wherein the heterologous tag comprises a HIS tag or a c-myc tag.

* * * * *

```
SEQUENCE LISTING


<160> NUMBER OF SEQ ID NOS: 9

<210> SEQ ID NO 1
<211> LENGTH: 257
<212> TYPE: PRT
<213> ORGANISM: Homo sapiens

<400> SEQUENCE: 1

Ser Gly Glu Pro Pro Lys Ser Gly Asp Arg Ser Gly Tyr Ser Ser Pro
1               5                   10                  15

Gly Ser Pro Gly Thr Pro Gly Ser Arg Ser Arg Thr Pro Ser Leu Pro
            20                  25                  30

Thr Pro Pro Thr Arg Glu Pro Lys Lys Val Ala Val Val Arg Thr Pro
        35                  40                  45

Pro Lys Ser Pro Ser Ser Ala Lys Ser Arg Leu Gln Thr Ala Pro Val
    50                  55                  60

Pro Met Pro Asp Leu Lys Asn Val Lys Ser Lys Ile Gly Ser Thr Glu
65                  70                  75                  80

Asn Leu Lys His Gln Pro Gly Gly Gly Lys Val Gln Ile Ile Asn Lys
                85                  90                  95

Lys Leu Asp Leu Ser Asn Val Gln Ser Lys Cys Gly Ser Lys Asp Asn
            100                 105                 110

Ile Lys His Val Pro Gly Gly Gly Ser Val Gln Ile Val Tyr Lys Pro
        115                 120                 125

Val Asp Leu Ser Lys Val Thr Ser Lys Cys Gly Ser Leu Gly Asn Ile
    130                 135                 140

His His Lys Pro Gly Gly Gly Gln Val Glu Val Lys Ser Glu Lys Leu
145                 150                 155                 160

Asp Phe Lys Asp Arg Val Gln Ser Lys Ile Gly Ser Leu Asp Asn Ile
                165                 170                 175

Thr His Val Pro Gly Gly Gly Asn Lys Lys Ile Glu Thr His Lys Leu
            180                 185                 190

Thr Phe Arg Glu Asn Ala Lys Ala Lys Thr Asp His Gly Ala Glu Ile
        195                 200                 205

Val Tyr Lys Ser Pro Val Val Ser Gly Asp Thr Ser Pro Arg His Leu
    210                 215                 220

Ser Asn Val Ser Ser Thr Gly Ser Ile Asp Met Val Asp Ser Pro Gln
225                 230                 235                 240

Leu Ala Thr Leu Ala Asp Glu Val Ser Ala Ser Leu Ala Lys Gln Gly
                245                 250                 255

Leu


<210> SEQ ID NO 2
<211> LENGTH: 64
<212> TYPE: PRT
<213> ORGANISM: Homo sapiens

<400> SEQUENCE: 2

Arg Val His Gly Lys Val Pro Ser His Leu Leu Arg Ser Lys Ile Thr
1               5                   10                  15

Lys Pro Asn Val Tyr His Glu Ser Lys Leu Ala Ala Lys Glu Tyr Gln
            20                  25                  30
```

```
Ala Ala Lys Ala Arg Leu Phe Thr Ala Phe Ile Lys Ala Gly Leu Gly
        35                  40                  45

Ala Trp Val Glu Lys Pro Thr Glu Gln Asp Gln Phe Ser Leu Thr Pro
    50                  55                  60


<210> SEQ ID NO 3
<211> LENGTH: 573
<212> TYPE: PRT
<213> ORGANISM: Homo sapiens

<400> SEQUENCE: 3

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350
```

```
Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Val
    530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                565                 570
```

<210> SEQ ID NO 4
<211> LENGTH: 163
<212> TYPE: PRT
<213> ORGANISM: Homo sapiens

<400> SEQUENCE: 4

```
Ser Glu Pro Ala Gly Asp Val Arg Gln Asn Pro Cys Gly Ser Lys Ala
1               5                   10                  15

Cys Arg Arg Leu Phe Gly Pro Val Asp Ser Glu Gln Leu Ser Arg Asp
            20                  25                  30

Cys Asp Ala Leu Met Ala Gly Cys Ile Gln Glu Ala Arg Glu Arg Trp
        35                  40                  45

Asn Phe Asp Phe Val Thr Glu Thr Pro Leu Glu Gly Asp Phe Ala Trp
    50                  55                  60

Glu Arg Val Arg Gly Leu Gly Leu Pro Lys Leu Tyr Leu Pro Thr Gly
65                  70                  75                  80

Pro Arg Arg Gly Arg Asp Glu Leu Gly Gly Gly Arg Arg Pro Gly Thr
                85                  90                  95

Ser Pro Ala Leu Leu Gln Gly Thr Ala Glu Glu Asp His Val Asp Leu
            100                 105                 110

Ser Leu Ser Cys Thr Leu Val Pro Arg Ser Gly Glu Gln Ala Glu Gly
        115                 120                 125

Ser Pro Gly Gly Pro Gly Asp Ser Gln Gly Arg Lys Arg Arg Gln Thr
    130                 135                 140
```

Ser Met Thr Asp Phe Tyr His Ser Lys Arg Arg Leu Ile Phe Ser Lys
145 150 155 160

Arg Lys Pro

<210> SEQ ID NO 5
<211> LENGTH: 9
<212> TYPE: PRT
<213> ORGANISM: Homo sapiens

<400> SEQUENCE: 5

Cys Asp Ala Gly Arg Lys Gln Lys Cys
1 5

<210> SEQ ID NO 6
<211> LENGTH: 140
<212> TYPE: PRT
<213> ORGANISM: Homo sapiens

<400> SEQUENCE: 6

Glu Gln Lys Lys Arg Ala Leu Asp Val Ile Gln Ala Gly Lys Glu Tyr
1 5 10 15

Val Glu His Thr Val Lys Glu Arg Lys Lys Gln Leu Lys Lys Glu Gly
20 25 30

Lys Pro Thr Ile Val Glu Glu Asp Asp Pro Glu Leu Phe Lys Gln Ala
35 40 45

Val Tyr Lys Gln Thr Met Lys Leu Phe Ala Glu Leu Glu Ile Lys Arg
50 55 60

Lys Glu Arg Glu Ala Lys Glu Met His Glu Arg Lys Arg Gln Arg Glu
65 70 75 80

Glu Glu Ile Glu Ala Gln Glu Lys Ala Lys Arg Glu Arg Glu Trp Gln
85 90 95

Lys Asn Phe Glu Glu Ser Arg Asp Gly Arg Val Asp Ser Trp Arg Asn
100 105 110

Phe Gln Ala Asn Thr Lys Gly Lys Lys Glu Lys Lys Asn Arg Thr Phe
115 120 125

Leu Arg Pro Pro Lys Val Lys Met Glu Gln Arg Glu
130 135 140

<210> SEQ ID NO 7
<211> LENGTH: 32
<212> TYPE: PRT
<213> ORGANISM: Homo sapiens

<400> SEQUENCE: 7

Ala Gln Asn Ile Thr Ala Arg Ile Gly Glu Pro Leu Val Leu Lys Cys
1 5 10 15

Lys Gly Ala Pro Lys Lys Pro Pro Gln Arg Leu Glu Trp Lys Leu Asn
20 25 30

<210> SEQ ID NO 8
<211> LENGTH: 84
<212> TYPE: PRT
<213> ORGANISM: Homo sapiens

<400> SEQUENCE: 8

Met Lys Asp Lys Gln Lys Lys Lys Lys Glu Arg Thr Trp Ala Glu Ala
1 5 10 15

Ala Arg Leu Val Leu Glu Asn Tyr Ser Asp Ala Pro Met Thr Pro Lys
20 25 30

-continued

```
Gln Ile Leu Gln Val Ile Glu Ala Glu Gly Leu Lys Glu Met Ser Gly
        35                  40                  45

Thr Ser Pro Leu Ala Cys Leu Asn Ala Met Leu His Ser Asn Ser Arg
    50                  55                  60

Gly Gly Glu Gly Leu Phe Tyr Lys Leu Pro Gly Arg Ile Ser Leu Phe
65                  70                  75                  80

Thr Leu Lys Arg


<210> SEQ ID NO 9
<211> LENGTH: 160
<212> TYPE: PRT
<213> ORGANISM: Homo sapiens

<400> SEQUENCE: 9

Met Glu Thr Met Lys Ser Lys Ala Asn Cys Ala Gln Asn Pro Asn Cys
1               5                   10                  15

Asn Ile Met Ile Phe His Pro Thr Lys Glu Glu Phe Asn Asp Phe Asp
            20                  25                  30

Lys Tyr Ile Ala Tyr Met Glu Ser Gln Gly Ala His Arg Ala Gly Leu
        35                  40                  45

Ala Lys Ile Ile Pro Pro Lys Glu Trp Lys Ala Arg Glu Thr Tyr Asp
    50                  55                  60

Asn Ile Ser Glu Ile Leu Ile Ala Thr Pro Leu Gln Gln Val Ala Ser
65                  70                  75                  80

Gly Arg Ala Gly Val Phe Thr Gln Tyr His Lys Lys Lys Lys Ala Met
                85                  90                  95

Thr Val Gly Glu Tyr Arg His Leu Ala Asn Ser Lys Lys Tyr Gln Thr
            100                 105                 110

Pro Pro His Gln Asn Phe Glu Asp Leu Glu Arg Lys Tyr Trp Lys Asn
        115                 120                 125

Arg Ile Tyr Asn Ser Pro Ile Tyr Gly Ala Asp Ile Ser Gly Ser Leu
    130                 135                 140

Phe Asp Glu Asn Thr Lys Gln Trp Asn Leu Gly His Leu Gly Thr Ile
145                 150                 155                 160
```